(12) United States Patent  
Yamaguchi et al.

(10) Patent No.: US 7,993,935 B2
(45) Date of Patent: Aug. 9, 2011

(54) TEST STRIP FOR IMMUNOCHROMATOGRAPHY

(75) Inventors: Haruki Yamaguchi, Kobe (JP);
Takehiro Hasegawa, Kobe (JP);
Takeshi Imoarai, Kobe (JP)

(73) Assignee: Sysmex Corporation, Tokyo (JP)

( * ) Notice: Subject to any disclaimer, the term of this patent is extended or adjusted under 35 U.S.C. 154(b) by 458 days.

(21) Appl. No.: 11/325,349

(22) Filed: Jan. 5, 2006

(65) Prior Publication Data

US 2006/0148097 A1   Jul. 6, 2006

(30) Foreign Application Priority Data

Jan. 6, 2005 (JP) ................................. 2005-001182

(51) Int. Cl.
*G01N 33/53* (2006.01)

(52) U.S. Cl. ........ 436/514; 436/518; 436/169; 436/530; 436/805; 436/810; 435/7.1; 435/287.7; 435/287.8; 435/287.9; 435/805; 435/810; 435/970; 422/420; 422/421; 422/424; 422/425; 422/430

(58) Field of Classification Search ................... 436/514, 436/518, 169, 530, 805, 810; 435/7.1, 287.7, 435/287.8, 287.9, 805, 810, 970; 422/56, 422/57, 61

See application file for complete search history.

(56) References Cited

U.S. PATENT DOCUMENTS

| | | | |
|---|---|---|---|
| 5,559,041 A * | 9/1996 | Kang et al. ..................... 436/518 |
| 6,177,281 B1 | 1/2001 | Manita |
| 6,180,417 B1 | 1/2001 | Hajizadeh et al. |
| 6,194,221 B1 | 2/2001 | Rehg et al. |
| 6,271,046 B1 | 8/2001 | Chandler |
| 6,582,970 B1 | 6/2003 | Manita |
| 7,378,285 B2 * | 5/2008 | Lambotte et al. ............. 436/514 |

FOREIGN PATENT DOCUMENTS

| | | |
|---|---|---|
| EP | 0 516 095 A2 | 12/1992 |
| JP | 4-351962 A | 12/1992 |
| JP | 08-094618 A | 4/1996 |
| JP | 10-048212 A | 2/1998 |
| JP | 10-68730 A | 3/1998 |

OTHER PUBLICATIONS

Japanese Office Action dated Nov. 24, 2009 in corresponding Japanese Patent Application No. 2005-001182.

* cited by examiner

*Primary Examiner* — Bao Thuy L Nguyen
(74) *Attorney, Agent, or Firm* — Sughrue Mion, PLLC (57) ABSTRACT

A test strip for immunochromatography comprising a sample receiving member, a label holding member, and a chromatography membrane is described. The chromatography membrane has a first detection zone and a second detection zone. The second detection zone is formed by utilizing a blocking material and the second substance. A method for producing above the test strip is also described.

15 Claims, 3 Drawing Sheets

Fig.2

TEST STRIP FOR IMMUNOCHROMATOGRAPHY

TECHNICAL FIELD

The present invention relates to a test strip for detecting multiple analytes in a sample prepared on the basis of an antigen-antibody reaction.

BACKGROUND

As a method for immunologically detecting an analyte in a sample, immunochromatography is known. Immunochromatography is a method for detecting an analyte by an antigen-antibody reaction by using a test strip. In immunochromatography, an antibody or antigen fixed on the chromatography membrane, the analyte, and antibody or antigen bound to a labeling marker (labeled antibody or labeled antigen) are made reacted on the chromatography membrane on which the antibody or antigen has been fixed in a detection zone.

At the time when an analyte is detected by utilizing an immunochromatography, even a negative sample in which the analyte is not contained in a sample may be determined as a positive (false-positive) in some cases. As a causing factor of false-positive, it is estimated that a labeled antibody or labeled antigen is nonspecifically bound to the detection zone. In order to suppress false-positive by such a nonspecific reaction, a blocking material is used (Japanese Laid-Open Patent Publication No. 10-068730). According to this technology, after an antibody or antigen has been fixed on the chromatography membrane, the nonspecific reaction can be suppressed by immersing the chromatography membrane in a buffer containing the blocking material, and further drying. However, in the case where a chromatography membrane having multiple detection zones for detecting two or more types of analytes is used, even if the above-described technology is used, a nonspecific reaction can be generated, and resulted in false-positive. This is because the substance fixed on the detection zone located on the side of upstream of the development direction is trapped in the detection zone located on the side of downstream separated from the detection zone. Therefore, the development of a test strip in which a false-positive is not generated by a nonspecific reaction in the detection zone located on the side of downstream has been desired.

SUMMARY

The present invention provides a test strip for immunochromatography and a method for producing the test strip.

The scope of the present invention is defined solely by the appended claims, and is not affected to any degree by the statements within this summary.

A first aspect of the present invention relates to a test strip for immunochromatography for detecting a first analyte and a second analyte in a sample, comprising:
  a sample receiving member for receiving the sample;
  a label holding member for holding a first labeling substance specifically binding to the first analyte and a second labeling substance specifically binding to the second analyte; and
  a chromatography membrane comprising a first detection zone which comprises a first substance specifically binding to the first analyte and a second detection zone which comprises a blocking material and a second substance specifically binding to the second analyte,
wherein the second detection zone is formed by a mixture of the blocking material and the second substance, the sample receiving member is arranged in contact with the label holding member, and the chromatography membrane is arranged in contact with the sample receiving member, the label holding member, or both.

A second aspect of the present invention relates to a test strip for immunochromatography for detecting a first analyte and a second analyte in a sample, comprising:
  a sample receiving member for receiving the sample;
  a label holding member comprising a first labeling substance specifically binding to the first analyte, and a second labeling substance specifically binding to the second analyte; and
  a chromatography membrane comprising a first detection zone which comprises a first substance specifically binding to the first analyte, and a second detection zone which comprises a layer comprising a first blocking and a second substance specifically binding to the second analyte,
wherein the sample receiving member is arranged in contact with the label holding member, and the chromatography membrane is arranged in contact with the sample receiving member, the label holding member, or both.

A third aspect of the present invention relates to a method for producing a test strip for immunochromatography for detecting a first analyte and a second analyte in a sample, comprising steps of:
  forming a first detection zone on a chromatography membrane of the test strip by applying a first solution comprising a first substance specifically binding to the first analyte; and
  forming a second detection zone on the chromatography membrane by applying a second solution comprising a blocking material and a second substance specifically binding to the second analyte.

DESCRIPTION OF THE PREFERRED EMBODIMENTS

A test strip of the present embodiments is a test strip for detecting a first analyte and a second analyte in a sample. This test strip has a sample receiving member with which a sample contacts, a label holding member and a chromatography membrane. The label holding member holds a first labeling substance specifically binding to the first analyte by antigen-antibody reaction, and a second labeling substance specifically binding to the second analyte by antigen-antibody reaction.

The chromatography membrane has a first detection zone, and a second detection zone which is located on the downstream side of the first detection zone in sample development direction. A first substance is fixed in the first detection zone, and a second substance is fixed in the second detection zone. The first substance can specifically bind to the first analyte by antigen-antibody reaction, and the second substance can specifically bind to the second analyte by antigen-antibody reaction.

The second detection zone is formed by a mixture of a blocking material and the second substance. In the case where the first analyte is contained in a sample, it is detected in the first detection zone. In the case where the second analyte is contained in a sample, it is detected in the second detection zone.

Concerning with a conventionally utilized test strip which has been provided in multiple detection zones, in the case where a sample containing larger amount of an analyte trapped in the upstream side detection zone is utilized as a specimen, a nonspecific reaction may be generated in the downstream side detection zone. However, since the second detection zone of a test strip of the present embodiment has been prepared using a blocking material and the second substance, it can be suppressed that the first substance is released from the first detection zone and it is trapped in the second detection zone. Specifically, even in the case where a sample containing larger amount of the first analyte is utilized as a specimen, the analyte in the sample can be precisely detected by suppressing false-positive due to the nonspecific reaction.

Hereinafter, a test strip of the present embodiments will be explained with reference to the drawings.

Figure 1:
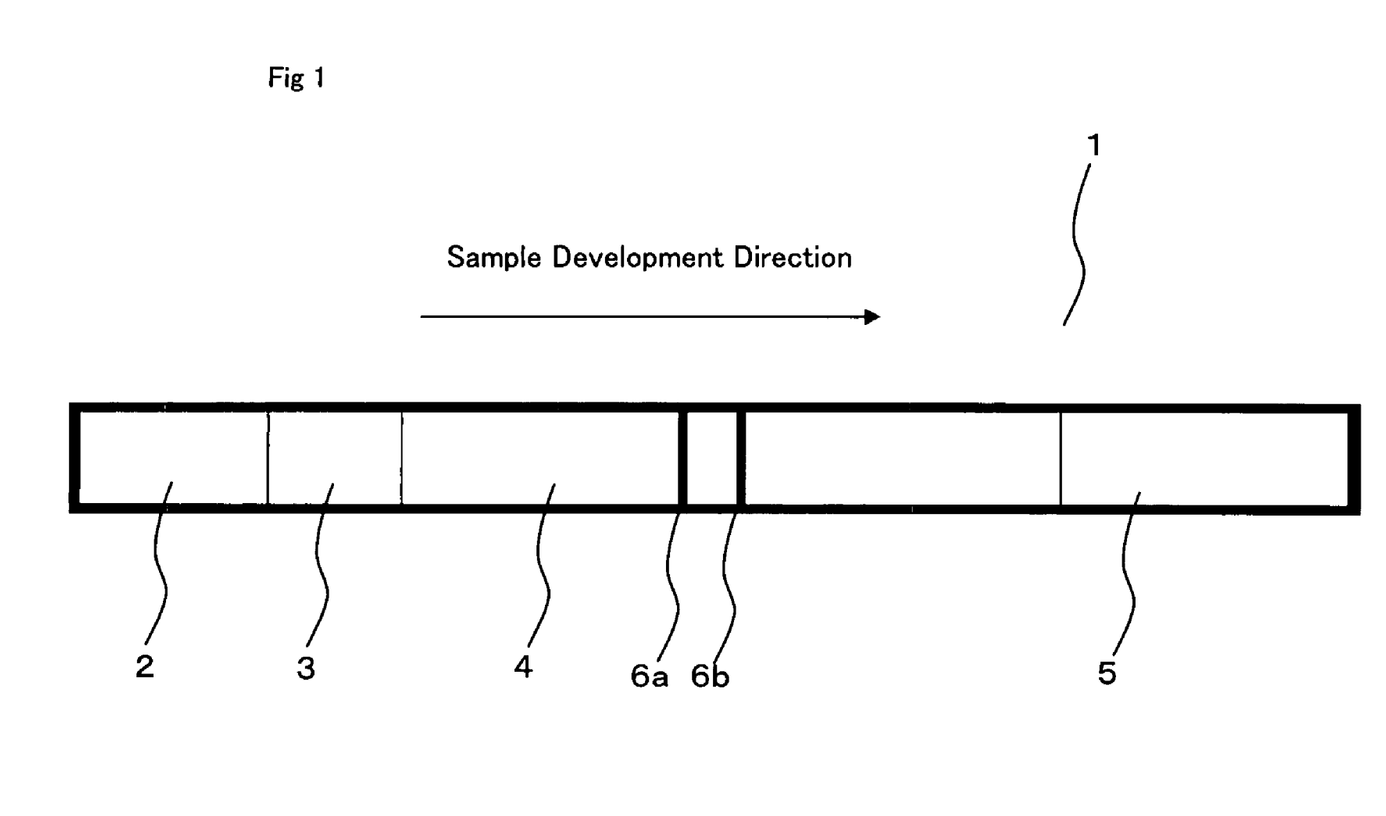
FIG. 1 shows a top plan view of a test strip 1.
Figure 2:
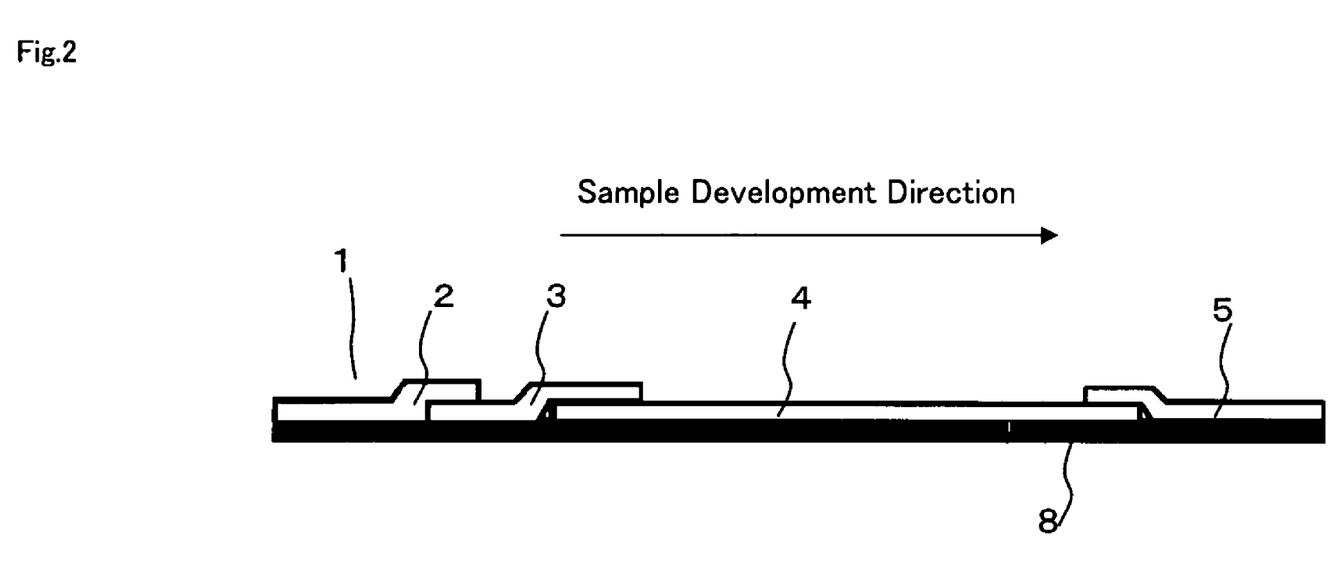
FIG. 2 shows a side elevation view of the test strip 1.

FIG. 1 is a top plan view of a test strip 1 according to one embodiment of the present invention. FIG. 2 is a side elevation view of the test strip 1. The test strip 1 is a test strip by which influenza A virus and influenza B virus in a sample are detected time by utilizing an immunochromatography. As a sample, nasal discharge, nasal swab, pharynx swab and the like can be utilized. The arrows of FIG. 1 and FIG. 2 indicate the development directions of the samples.

The test strip 1 is equipped with a sample receiving member 2, a label holding member 3, a chromatography membrane 4 and an absorbing member 5 in order from the upstream side of the sample development direction. The sample receiving member 2 is composed of rayon in a form of sheet. The label holding member 3 and the absorbing member 5 are composed of glass fiber in a form of sheet, respectively. The chromatography membrane 4 is composed of cellulose nitrate in a form of sheet.

The label holding member 3 holds a labeled anti-influenza A virus antibody (hereinafter, referred to as labeled anti-A antibody) and a labeled anti-influenza B virus antibody (hereinafter, referred to as labeled anti-B antibody). The labeled anti-A antibody has an anti-influenza A virus antibody (hereinafter, referred to as anti-A antibody) which is capable of binding specifically to influenza A virus antigen. In addition, the labeled anti-A antibody has a polystyrene latex particle which has been colored in blue as a label. A labeled anti-B antibody has an anti-influenza B virus antibody (hereinafter, referred to as anti-B antibody) which is capable of binding specifically to influenza B virus antigen. In addition, the labeled anti-B antibody has a polystyrene latex particle which has been colored in blue as a label.

The chromatography membrane 4 is equipped with a detection zone 6a for detecting influenza A virus (hereinafter, A virus detection zone 6a) and a detection zone 6b for detecting influenza B virus (hereinafter, referred to as B virus detection zone 6b). In the A virus detection zone 6a, an anti-influenza A virus antibody for fixation which is capable of binding specifically to influenza A virus antigen (hereinafter, referred to as anti-A antibody for fixation) has been fixed. In the B virus detection zone 6b, an anti-influenza B virus antibody which is capable of binding specifically to influenza B virus antigen (hereinafter, referred to as anti-B antibody for fixation) has been fixed.

As shown in FIG. 2, the sample receiving member 2, the label holding member 3, the chromatography membrane 4 and the absorbing member 5 have been adhered to the substrate 8 made of plastic, and these are coupled respectively so that the development of the sample due to capillary phenomenon is not ceased. The bottom surface at the downstream side of the label holding member 3 is disposed in contact with the top surface which is located on the side of upstream upper than the A virus detection zone 6a of the chromatography membrane 4. The bottom surface on the side of downstream of the sample receiving member 2 is disposed in contact with the top surface on the side of upstream of the label holding member 3. The bottom surface on the side of upstream of the absorbing member 5 is disposed in contact with the top surface on the side of downstream lower than the B virus detection zone 6b of the chromatography membrane 4.

The A virus detection zone 6a is prepared by applying a solution containing the anti-A antibody for fixation and bovine serum albumin (BSA).

The B virus detection zone 6b is prepared by applying a solution containing the anti-B antibody for fixation and bovine serum albumin (BSA).

The application of solution containing an antibody can be performed by utilizing a device. As a device, it is not particularly limited. For example, Dispensing and Spraying system XYZ series manufactured by BioDot, Inc. can be used.

Referring to the chromatography membrane 4, after the detection zone has been prepared by applying a solution containing BSA and an antibody, it is immersed in a solution containing BSA and further, is blocked.

In the present embodiment, the analyte is influenza virus. However, as an analyte, it is not particularly limited if it is a substance which generates an antigen-antibody reaction. For instance, cell such as a bacterium, a protist, a mycosis and the like, the other viruses, a protein, polysaccharides and the like can be the analyte. Concretely, influenza virus, parainfluenza virus, RS virus, mycoplasma pneumoniae, rotavirus, Calici virus, corona virus, adenovirus, enterovirus, herpes virus, human immunodeficiency virus, hepatitis virus, pathogenic virus of severe acute respiratory syndrome (SARS), *E. coli, staphylococcus aureus, streptococcus pneumoniae, streptococcus pyogenes, Plasmodium*, and the others such as digestive system diseases, central nervous system diseases, pathogens of a variety of diseases such as hemorrhagic fever and the like, metabolites thereof, carcinoembryonic antigen, tumor markers such as CYFRA and the like, hormones and the like are targets of detection. A test strip of the present embodiment can be utilized for the purpose of performing the diagnosis of diseases by detection two or more types of analytes out of the above-described pathogens and metabolites thereof. However, it is preferable that it is utilized for performing typing diagnosis of homogeneous analytes. As an example of typing diagnosis of homogeneous analytes, simultaneous detection of hepatitis A to E viruses and simultaneous detection of I type and II type human immunodeficiency virus and the like are listed.

In the present embodiment, the sample receiving member 2 is composed of rayon. However, the material is not particularly limited if it is a porous substance having water absorbing property which generates capillary phenomenon. For example, it is also possible to utilize glass fiber, polyester, polypropylene, polyethylene and the like.

The label holding member 3 and absorbing member 5 are composed of glass fiber. However, the material is not particularly limited if it is a porous substance having water absorbing property which generates capillary phenomenon. For example, it is also possible to utilize rayon, polyester, polypropylene, polyethylene and the like.

The chromatography membrane 4 is composed of cellulose nitrate. However, as a material for the chromatography membrane 4, the material is not particularly limited if it can fix an antigen and antibody, it is a porous water absorbing substance which generates capillary phenomenon and the liquid can be developed by a chromatography. For example, it is also possible that polyvinylidene fluoride, polyamide, poly(ethersulfone) and the like are utilized.

In the present embodiment, the A virus detection zone 6a and the B virus detection zone 6b are prepared using an antibody solution containing BSA as a blocking material, respectively. As a blocking material which is contained in this antibody solution, it is not particularly limited if it is a blocking material which does not generate an antigen-antibody reaction with respect to any one of influenza A virus antigen, influenza B virus antigen, labeled anti-A antibody, labeled anti-B antibody, anti-A antibody for fixation and anti-B antibody for fixation. Except for BSA, as a blocking material, a serum albumin such as that of goat, bird or the like, globulin, casein, gelatin, skimmed milk, polyvinyl alcohol, polyvinylpyrrolidone and the like can be exemplified. These blocking materials can be utilized singly or two or more species can be also utilized in combination. Moreover, when a serum collected from animals such as bovine, goat, bird and the like are added to the above-described antibody solution instead of BSA, a similar effect can be obtained. Among the blocking materials described above, it is preferable that BSA, casein, gelatin, or skimmed mild is used.

In the present embodiment, the A virus detection zone 6a is prepared by utilizing an antibody solution containing BSA as a blocking material. However, the A virus detection zone 6a may be prepared by utilizing an antibody solution not containing a blocking material.

In the present embodiment, as for the chromatography membrane 4, after the detection zone has been prepared by applying a solution containing BSA and an antibody, it is immersed in a solution containing BSA as a blocking material and is blocked. However, the blocking may be performed by utilizing a solution containing the other blocking material described above which is not BSA. Moreover, a solution containing two or more species of blocking materials out of the above-described blocking materials may be used.

In the present embodiment, as for the chromatography membrane 4, after the detection zone has been prepared by applying a solution containing BSA and an antibody, it is immersed in a buffer containing BSA; however, this blocking treatment may not be performed.

Moreover, as an antibody utilized for the present embodiment, a polyclonal antibody or monoclonal antibody may be available (Kohler & Milstein, 1975, Nature, Vol. 256, 495), these may be singly used or used in combination. It should be noted that the term "antibody" used in the present specification also includes a fragment of an antibody and derivatives thereof. As a fragment of an antibody and derivatives thereof, concretely, Fab, Fab', F(ab)$_2$ and sFv fragment and the like (Blazar et al., 1997, J. Immunol., 159: 5821-5833 and Bird et al., 1988, Science, 242: 423-426) are exemplified. As for subclass of antibody, it is not limited to IgG, and it may be IgM or the like.

If it is an antibody which can recognize the same species of antigen, antigen coupling section, that is, paratope of the labeled anti-A antibody and the paratope of anti-A antibody for fixation may be the same with each other or different from each other. Similarly, the paratope of the labeled anti-B antibody and paratope of anti-B antibody for fixation may be the same with each other or different from each other.

Moreover, in the present embodiment, as a carrier particle, polystyrene latex particle is used. However, it is not particularly limited if it is a particle which can bind to an antigen or antibody. For example, latex particle other than polystyrene, a colloidal metal particle such as gold, silver, platinum and the like, a colloidal metal oxide particle such as iron oxide and the like can be used. A latex particle can be obtained by polymerizing or co-polymerizing a variety of monomers. For example, as a monomer, polymerizable unsaturated aromatics (for example, chlorstyrene, alpha-methyl styrene, divinylbenzene, vinyl toluene and the like), polymerizable unsaturated carboxylic acids (for example, (meth)acrylic acid, itaconic acid, maleic acid, fumaric acid and the like), polymerizable carboxylates (for example, methyl(meth)acrylate, ethyl(meth)acrylate, (meth)acrylic acid-n-butyl, (meth)acrylic acid-2-hydroxyethyl, glycidyl(meth)acrylate, ethylene glycol-di-(meth)acrylate, tribromophenyl(meth)acrylate and the like), unsaturated amide carboxylates, (for example (meth)acrylonitrile, (meth)acrolein, (meth)acrylamide, N-methylol(meth)acrylamide, methylene-bis(meth)acrylamide, butadiene, isoprene, vinyl acetate, vinylpyridine, N-vinyl pyrrolidone, vinyl chloride, vinylidene chloride, vinyl bromide and the like), polymerizable unsaturated nitriles, halogenated vinyls, conjugated dienes and the like can be exemplified, and one species or two species or more of these out of these described above can be used.

Moreover, a control zone may be prepared. The control zone is for recognizing whether or not the sample was appropriately developed. The control zone is preferably prepared at the downstream side lower than the B virus detection zone 6b of the chromatography membrane 4.

In the control zone, a substance for control is fixed. A labeling substance for control which is capable of binding to a substance for control is held on the label holding member 3. As a substance for control, for example, biotin (or avidin) can be used. In this case, as a labeling substance for control, labeling avidin (or labeling biotin) having a colored carrier particle and avidin (or biotin) can be used. A labeling avidin (or labeling biotin) held on the label holding member 3 moves towards the downstream side in the sample development direction accompanying with the sample by capillary phenomenon at the time when the sample is developed, and when it has reached to the control zone, it binds to biotin (or avidin) which has been fixed and trapped in the control zone, and the control zone is colored. Whether or not the sample is appropriately developed can be confirmed by observing this color. Moreover, hapten (or anti-hapten antibody) is fixed as a substance for control in the control zone, and the anti-hapten body (or hapten) which has been labeled with a colored carrier particle may be held by the label holding member 3 as a labeling substance for control.

Figure 3A:
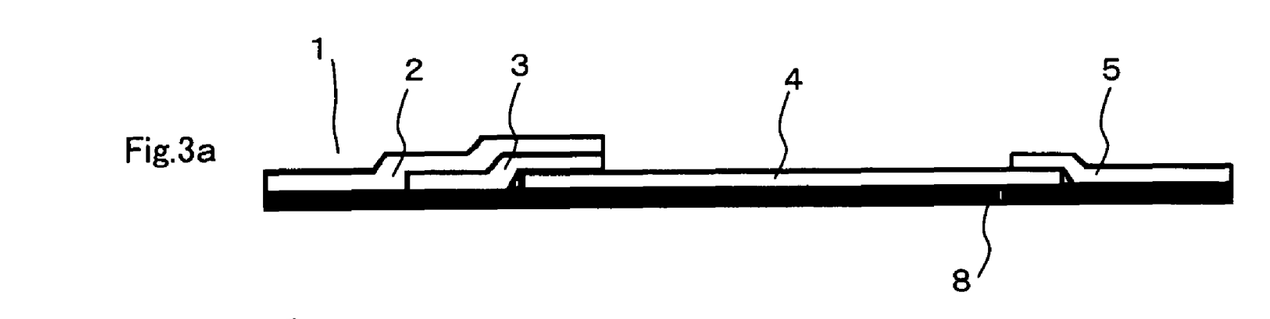
FIG. 3(a) shows a side elevation view of the test strip 1 according to one embodiment of the present invention.

Moreover, as shown in FIG. 3a, the test strip 1 may have a structure in which the bottom surface located on the side of the downstream of the sample receiving member 2 is in contact with the entire top surface of the label holding member 3.

Figure 3B:
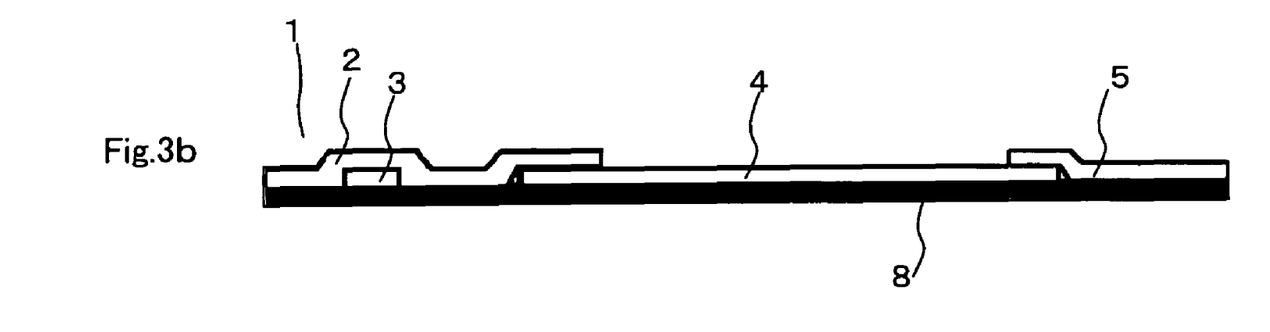
FIG. 3(b) shows a side elevation view of the test strip 1 according to one embodiment of the present invention.

Moreover, as shown in FIG. 3b, the test strip 1 may have a structure in which the chromatography membrane 4 and the label holding member 3 are disposed via the gap, the bottom surface of the sample receiving member 2 covers the label holding member 3, and the bottom surface located on the side of the downstream of the sample receiving member 2 is in contact with the top surface located on the side of the upstream upper than the A virus detection zone 6a of the chromatography membrane 4.

Figure 3C:
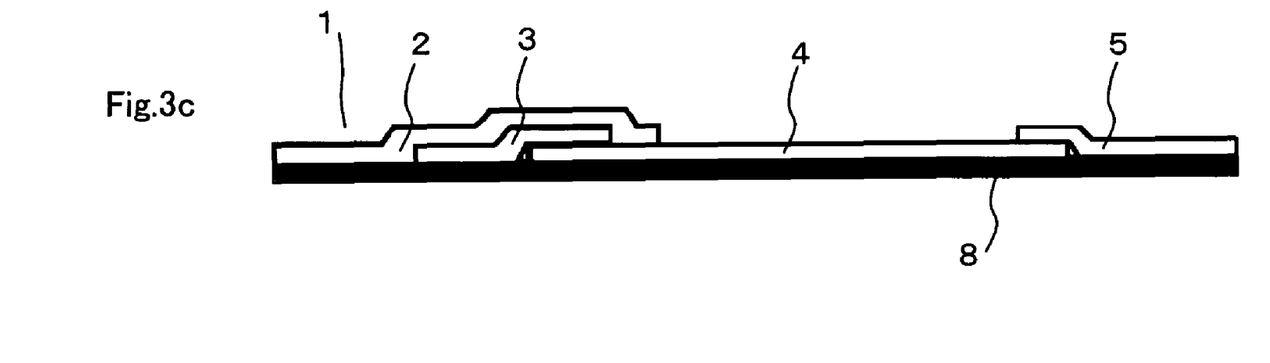
FIG. 3(c) shows a side elevation view of the test strip 1 according to one embodiment of the present invention.

Moreover, as shown in FIG. 3c, the test strip 1 may have a structure in which the bottom surface of the sample receiving member 2 is in contact with the entire top surface of the label holding member 3, the terminal located on the side of the downstream of the sample receiving member 2 is in contact with one portion located on the side of the upstream upper than the A virus detection zone 6a of the chromatography membrane 4.

Moreover, in the present embodiment, whether or not the sample contains an analyte is determined by detecting an antigen in the sample using a labeled antibody and an antibody for fixation. However, whether or not the sample contains an analyte may be determined by detecting an antibody in the sample using a labeled antigen and an antigen for fixation. In this case, a carrier particle bound to an antigen for generating an antigen-antibody reaction with an antibody which is an analyte in the sample is used as labeled antigen, and the antigen for fixation which generates an antigen-antibody reaction with this antibody is fixed in the detection zone of the chromatography membrane 4.

Hereinafter, the detection of influenza A virus and influenza B virus using the test strip 1 will be explained.

It is preferable that the sample collected from the living organism is subjected to the pretreatment. Influenza virus becomes a state where it is more suitable for detection and the detection sensibility can be enhanced by performing the pretreatment. The pretreatment can be performed by adding the sample in the pretreatment liquid and filtering with a filter. As a pretreatment liquid, an aqueous solution containing non-ionic surfactant, alkali metal ion and the like can be utilized.

The sample supplied to the detection of an analyte (hereinafter, referred to as sample to be detected) is added to the sample receiving member 2 of the test strip 1. At the time when the sample to be detected is added, the sample to be detected moves towards downstream side from the sample receiving member 2 by capillary phenomenon and reaches to the label holding member 3. The sample to be detected moves to the chromatography membrane 4 accompanying with a labeled antibody which is carried by the label holding member 3. At the time when the sample to be detected and labeled antibody reaches to the A virus detection zone 6a of the chromatography membrane 4, in the case where influenza A virus exists in the sample to be detected, influenza A virus antigen binds to a labeled anti-A antibody and anti-A antibody for fixation in a sandwiched form in the A virus detection zone. Since the labeled anti-A antibody is equipped with the blue polystyrene latex particle, at the time when it is trapped in the A virus detection zone, the A virus detection zone 6a turns blue. Whether or not influenza A virus exists in the sample to be detected can be determined by determining whether or not this color is observed. Similarly, at the time when the sample to be detected and labeled antibody reach to the B virus detection zone 6b, in the case where influenza B virus exists in the sample to be detected, influenza B virus antigen binds to the labeled anti-B antibody and anti-B antibody for fixation in a sandwiched form in the B virus detection zone. Since the labeled anti-B antibody is equipped with the blue polystyrene latex particle, at the time when it is trapped in the B virus detection zone 6b, the B virus detection zone 6b turns blue. Whether or not influenza B virus exists in the sample can be determined by determining whether or not this color is observed. The labeled antibody which has not been trapped by the sample to be detected and the respective detection zones is absorbed by the absorbing member 5 which is located at the lowest location of the downstream side of the test strip 1.

EXPERIMENTS (Preparation of Chromatography Membrane A)

A cellulose nitrate film (manufactured by Nihon Millipore, K. K.) was used for chromatography membrane A.

Anti-influenza A virus antibody for fixation was fixed in the A virus detection zone. The anti-A antibody solution for fixation (pH 7.0) containing PBS, 2.0 mg/mL of the anti-influenza A virus antibody for fixation and 1.0 mg/mL of BSA was applied to the cellulose nitrate film in a linear form, and these lines were made the A virus detection zone.

The anti-influenza B virus antibody for fixation was fixed in the B virus detection zone. The anti-B antibody solution for fixation (pH 7.0) containing PBS, 1.5 mg/mL of anti-influenza B virus antibody for fixation was applied in a linear form lower at the downstream side than the A virus detection zone of the above-described cellulose nitrate film, and these lines were made B virus detection zone.

The anti-A antibody solution for fixation and the anti-B antibody solution for fixation were applied to the cellulose nitrate film using "XYZ 3000" manufactured by BioDott, Inc.

After the anti-A antibody solution for fixation and the anti-B antibody solution for fixation were applied to the cellulose nitrate film, the cellulose nitrate film was dried. Subsequently, it was blocking treated by immersing it in the blocking solution (monosodium phosphate, 10 mM; sodium azide, 0.1 w/v %; BSA, 1.0 w/v %; pH 7.0), furthermore dried and it was made chromatography membrane A.

(Preparation of Label Holding Member)

The blue polystyrene latex particle having the average particle diameter of 0.3 µm was added to PBS (pH 8.0), and further glutaraldehyde was added so that the final concentration is 1.0 w/v %, and agitated at 25° C. for one hour. The supernatant was removed by centrifuging the mixture which has been agitated, and PBS (pH 8.0) was added to the deposit. Next, polystyrene latex particle was dispersed, 100 µg/mL of monoclonal antibody which is capable of binding to the influenza A virus antigen was added, and it was agitated at 25° C. for two hours. This was centrifuged and the supernatant was removed. After PBS (pH 8.0) containing 10 w/v % BSA was added to the obtained deposit and mixed and dispersed, it was stood at rest at 37° C. overnight. The mixture prepared in this way was centrifuged and the supernatant was removed, and PBS (pH 8.0) containing 5w/v % BSA was added to the deposit. After it was mixed and dispersed, it was filtered by a 0.8 µm mesh filter, and the obtained filtered liquid was made labeled anti-A antibody solution.

The labeled anti-B antibody solution was prepared similarly to the labeled anti-A antibody solution except that monoclonal antibody which is capable of binding to an influenza B virus antigen is used instead of a monoclonal antibody which is capable of binding to the influenza A virus antigen.

The labeled anti-A antibody and labeled anti-B antibody which were prepared in the above-described way were mixed at the ratio of 1:1, and after it was immersed in a glass fiber, it was dried and a label holding member was obtained.

(Preparation of Test Strip A)

As the chromatography membrane 4 shown in FIG. 2, the test strip A was prepared using the chromatography membrane A.

(Preparation of Chromatography Membranes B and C)

The chromatography membrane B was prepared similarly to the chromatography membrane A except that the B virus detection zone is prepared by utilizing an anti-B antibody solution for fixation containing PBS, 1.5 mg/mL of anti-influenza B virus antibody for fixation and 1.0 mg/mL BSA.

The chromatography membrane C was prepared similarly to the chromatography membrane A except that the B virus detection zone is prepared by utilizing an anti-B antibody solution for fixation containing PBS, 1.5 mg/mL of anti-influenza B virus antibody for fixation and 2.0 mg/mL BSA.

(Preparation of Test Strips B and C)

The test strip B was prepared by utilizing the chromatography membrane B as the chromatography membrane 4 shown in FIG. 2.

The test strip C was prepared by utilizing the chromatography membrane C as the chromatography membrane 4 shown in FIG. 2.

Experiment 1

<Effect Due to Addition of BSA to Anti-B Antibody Solution for Fixation>

(Detection of Influenza Virus Using Test Strips A-C)

As a sample, the negative sample which contains neither influenza A virus nor influenza B virus, the influenza A virus weakly positive sample (sample 1), and the influenza A virus strongly positive sample (sample 2) were used.

Next, these samples were subjected to the pretreatment. The sample to be detected was obtained by mixing the sample and the pretreatment liquid (pH 7.8) containing 0.3 w/v % Nonidet P-40 (trade name of polyoxyethylene(9)octylphenylether), and filtering the mixture of the sample and the pretreatment liquid using a filter. Pretreated negative sample is referred to as negative sample to be detected. Pretreated sample 1 is referred to as sample to be detected 1. Pretreated Sample 2 is Referred to as Sample to be Detected 2.

These samples to be detected were added to the sample receiving members of the test strips A-C, respectively, and the detection of influenza virus was performed. The results are indicated in Table 1.

if any one of test strips were used, and the B virus detection zone was not turned blue. Specifically, it was determined that influenza A virus was positive.

In the case where the sample to be detected 2 was used as a specimen, the A virus detection zone was deeply turned blue even if any one of test strips were used, and it was determined that influenza A virus is strongly positive. However, although in the test strip A, the sample to be detected 2 not containing influenza B virus was used as a specimen, the B virus detection zone was turned blue. Concerning with this phenomenon which is generated at the time when the sample containing influenza A virus in a high concentration is used, it is considered that it is a false-positive generated by the procedure that the anti-A antibody for fixation is released from the A virus detection zone and it is trapped in the B virus detection zone accompanying with influenza A virus antigen.

In the case where the sample to be detected 2 was used as a specimen in the test strips B and C, the B virus detection zone was not turned blue, and the detection of influenza virus was precisely performed. From the fact, it was clarified that the false-positive reaction in the B virus detection zone of the test strips B and C can be suppressed by preparing the B virus detection zone of the test strips B and C using anti-B antibody solution for fixation containing BSA.

Experiment 2

<Effect Due to Addition of BSA to Anti-A Antibody Solution for Fixation>

It was examined utilizing test strip B what kind of effect is obtained in the case where the negative sample was used by preparing the A virus detection zone using anti-A antibody solution for fixation to which BSA was added. As a control, the test strip D was used. The test strip D was prepared similarly to the test strip A except that A virus detection zone was prepared by utilizing anti-A antibody solution for fixation not containing BSA.

For detection, the negative samples to be detected 1-40 were used as specimens.

TABLE 1

| | BSA concentration (mg/mL) of anti-B antibody solution for fixation | Negative sample to be detected | | Sample to be detected 1 | | Sample to be detected 2 | |
|---|---|---|---|---|---|---|---|
| | | A virus detection zone | B virus detection zone | A virus detection zone | B virus detection zone | A virus detection zone | B virus detection zone |
| Test strip A | 0.0 | − | − | + | − | +++ | + |
| Test strip B | 1.0 | − | − | + | − | +++ | − |
| Test strip C | 2.0 | − | − | + | − | +++ | − |

In Table 1, it is indicated that the more the number of the symbol + is, the stronger the color is in the detection zone, that is, the degree of positive is strong.

The symbol − indicates that the color was not observed in the detection zone, that is, it is negative.

It is indicated from Table 1 that in the case where a negative sample to be detected was used as a specimen, even if any one of the test strips is used, influenza virus was not detected in the respective detection zone.

In the case where the sample to be detected 1 was used as a specimen, the A virus detection zone was turned blue even The results are indicated in Table 2.

TABLE 2

| negative sample | Test strip D | Test strip B |
|---|---|---|
| 1 | − | − |
| 2 | − | − |
| 3 | − | − |
| 4 | − | − |
| 5 | − | − |

TABLE 2-continued

| negative sample | Test strip D | Test strip B |
|---|---|---|
| 6 | − | − |
| 7 | − | − |
| 8 | − | − |
| 9 | − | − |
| 10 | − | − |
| 11 | − | − |
| 12 | − | − |
| 13 | − | − |
| 14 | − | − |
| 15 | w | − |
| 16 | − | − |
| 17 | − | − |
| 18 | − | − |
| 19 | − | − |
| 20 | − | − |
| 21 | − | − |
| 22 | w | − |
| 23 | − | − |
| 24 | − | − |
| 25 | − | − |
| 26 | − | − |
| 27 | − | − |
| 28 | − | − |
| 29 | − | − |
| 30 | − | − |
| 31 | − | − |
| 32 | − | − |
| 33 | − | − |
| 34 | − | − |
| 35 | − | − |
| 36 | − | − |
| 37 | − | − |
| 38 | − | − |
| 39 | − | − |
| 40 | − | − |

In Table 2, the symbol w indicates that thin coloration was observed in the detection zone, that is, it is weakly positive.

The symbol − indicates that the coloration was not observed in the detection zone, that is, it is negative.

As indicated in Table 2, in two specimens out of the negative samples to be detected 1-40 in the test strip D, the thin coloration was observed in the A virus detection zone, This a false-positive generated by nonspecific reaction in the A virus detection zone, However, the coloration was not observed in all of the specimens in the test strip B, and the false-positive could be suppressed.

From the results described above, it was clarified that the false-positive generated in the A virus detection zone can be suppressed, in the case where the negative sample to be detected was used as a specimen, by preparing the A virus detection zone using anti-A antibody solution for fixation containing BSA.

Experiment 3

<Effect Due to Addition of Blocking Material Except BSA to Anti-B Antibody Solution for Fixation>

It was validated what kind of effect is obtained by preparing the B virus detection zone using anti-B antibody solution for fixation to which blocking material except BSA was added.

The test strip E was prepared similarly to the test strip A except that the B virus detection zone was prepared by utilizing an anti-B antibody solution for fixation containing PBS, 1.5 mg/mL of anti-influenza B virus antibody for fixation and 1.0 mg/mL of casein.

The test strip F was prepared similarly to the test strip A except that the B virus detection zone was prepared by utilizing an anti-B antibody solution for fixation containing PBS, 1.5 mg/mL of anti-influenza B virus antibody for fixation and 1.0 mg/mL of gelatin.

The test strip G was prepared similarly to the test strip A except that the B virus detection zone was prepared by utilizing an anti-B antibody solution for fixation containing PBS, 1.5 mg/mL of anti-influenza B virus antibody for fixation and 1.0 mg/mL of skimmed milk.

Here, the detection of influenza virus of the negative sample to be detected, the sample to be detected 1 and the sample to be detected 2 was performed by utilizing the test strips E-G, and further, as a control, the test strip D.

The results are indicated in Table 3.

TABLE 3

| | Negative sample to be detected | | Sample to be detected 1 | | Sample to be detected 2 | |
|---|---|---|---|---|---|---|
| | A virus detection zone | B virus detection zone | A virus detection zone | B virus detection zone | A virus detection zone | B virus detection zone |
| Test strip D | − | − | + | − | +++ | w |
| Test strip E | − | − | + | − | +++ | ± |
| Test strip F | − | − | + | − | +++ | ± |
| Test strip G | − | − | + | − | +++ | ± |

In Table 3, it is indicated that the more the number of the symbol + is, the stronger the coloration is in the detection zone, that is, the degree of positive is strong.

The symbol w indicates that thin coloration was observed in the detection zone, that is, it is weakly positive.

The symbol ± indicates that extremely thin coloration was observed in the detection zone.

The symbol − indicates that the coloration was not observed in the detection zone, that is, it is negative.

As indicated in Table 3, influenza virus was not detected in the respective detection zones in the case where the negative sample to be detected was used as a specimen even if any one of test strips was used.

In the case where the sample to be detected 1 was used as a specimen, even if any one of test strips was used, the A virus detection zone was turned blue and the B virus detection zone was not turned blue. Specifically, it was determined that influenza A virus is positive.

In the case where the sample to be detected 2 was used as a specimen, even if any one of test strips was used, the A virus detection zone was densely turned blue, and it was determined that influenza A virus is strongly positive. However, in the test strip D used as a control, the B virus detection zone was turned blue, and it represented false-positive. On the other hand, in the test strips E-G, the B virus detection zone was turned blue. However, the coloration was much thinner than the coloration in the test strip A. It was clarified that from the results described above, false-positive reaction in the B virus detection zone can be suppressed by preparing the B virus detection zone using anti-B antibody solution for fixation containing casein, gelatin or skimmed milk.

What is claimed is:

1. A test strip for immunochromatography for detecting a first analyte and a second analyte in a sample, comprising:
    a sample receiving member for receiving the sample;
    a label holding member for holding a first labeling substance specifically binding to the first analyte and a second labeling substance specifically binding to the second analyte; and
    a chromatography membrane comprising a first detection zone which comprises a first substance specifically binding to the first analyte and a second detection zone which comprises a blocking material and a second substance specifically binding to the second analyte,
    wherein the second detection zone is formed by a mixture of the blocking material and the second substance, the sample receiving member is arranged in contact with the label holding member, and the chromatography membrane is arranged in contact with the sample receiving member, the label holding member, or both,
    wherein the chromatography membrane is blocked by immersing in a solution comprising the blocking material after forming the first detection zone and the second detection zone,
    wherein an amount of the blocking material included in the second detection zone is larger than an amount of the blocking material included in the chromatography membrane other than the second detection zone,
    and wherein the blocking material is selected from the group consisting of globulin, albumin, casein, gelatin, skimmed milk, polyvinyl alcohol, polyvinylpyrrolidone and a serum collected from animals.

2. The test strip according to claim 1, wherein the second detection zone is formed by applying a solution comprising the blocking material and the second substance.

3. The test strip according to claim 1, wherein the first detection zone is formed by applying a solution comprising the blocking material and the first substance,
    wherein an amount of the blocking material included in the first detection zone and the second detection zone are larger than an amount of the blocking material included in the chromatography membrane other than the first detection zone and the second detection zone.

4. The test strip according to claim 1, wherein the sample receiving member is composed of a material selected from the group consisting of rayon, glass fiber, polypropylene, polyester, and polyethylene, the label holding member is composed of a material selected from the group consisting of rayon, glass fiber, polypropylene, polyester, and polyethylene, and the chromatography membrane is composed of a material selected from the group consisting of cellulose nitrate, polyvinylidene fluoride, polyamide, and poly(ethersulfone).

5. The test strip according to claim 1, wherein the blocking material is bovine serum albumin (BSA).

6. The test strip according to claim 1, wherein the first substance specifically binding to the first analyte is selected from the group consisting of a virus, a bacterium, a protist, a mycosis, a tumor marker and a hormone, and the second substance specifically binding to the second analyte is selected from the group consisting of a virus, a bacterium, a protist, a mycosis, a tumor marker and a hormone.

7. The test strip according to claim 1, wherein the first substance specifically binds to influenza A virus and the second substance specifically binds to influenza B virus.

8. The test strip according to claim 1, wherein the second substance specifically binds to influenza A virus and the first substance specifically binds to influenza B virus.

9. The test strip according to claim 1, wherein the first labeling substance comprises a colored latex particle and a third substance specifically binding to the first analyte, and the second labeling substance comprises a colored latex particle and a fourth substance specifically binding to the first analyte.

10. The test strip according to claim 9, wherein the first substance, the second substance, the third substance and the fourth substance are antibodies.

11. A method for producing a test strip for immunochromatography according to claim 1 for detecting a first analyte and a second analyte in a sample, comprising steps of:
    forming a first detection zone on a chromatography membrane of the test strip by applying a first solution comprising a first substance specifically binding to the first analyte; and
    forming a second detection zone on the chromatography membrane by applying a second solution comprising a blocking material and a second substance specifically binding to the second analyte.

12. The method according to claim 11, wherein the test strip comprises a sample receiving member, a label holding member, and the chromatography membrane.

13. The method according to claim 11, further comprising a step of forming the label holding member which holds:
    a first labeling substance specifically binding to the first analyte; and
    a second labeling substance specifically binding to the second analyte.

14. The method according to claim 11, wherein the first solution comprises the first substance and the blocking material.

15. The method according to claim 11, further comprising a step of immersing the chromatography membrane in a third solution containing the blocking material, after forming the first detection zone and the second detection zone.

* * * * *